(12) United States Patent
Hill

(10) Patent No.: US 8,453,838 B2
(45) Date of Patent: Jun. 4, 2013

(54) SYRINGE PISTON NEST FOR THE MANUFACTURE OF PRE FILLED SYRINGE

(75) Inventor: W. Edward Hill, Morgantown, PA (US)

(73) Assignee: West Pharmaceutical Services, Inc., Exton, PA (US)

( * ) Notice: Subject to any disclaimer, the term of this patent is extended or adjusted under 35 U.S.C. 154(b) by 33 days.

(21) Appl. No.: 12/999,668

(22) PCT Filed: Oct. 27, 2009

(86) PCT No.: PCT/US2009/062226
§ 371 (c)(1),
(2), (4) Date: Dec. 17, 2010

(87) PCT Pub. No.: WO2010/062602
PCT Pub. Date: Jun. 3, 2010

(65) Prior Publication Data
US 2011/0192756 A1     Aug. 11, 2011

Related U.S. Application Data

(60) Provisional application No. 61/108,950, filed on Oct. 28, 2008.

(51) Int. Cl.
*A61B 17/06* (2006.01)
(52) U.S. Cl.
USPC .............. 206/438; 206/499; 211/40; 211/74; 422/500; 422/526; 422/552; 422/553; 604/192
(58) Field of Classification Search
USPC ..... 206/438, 443, 366, 486, 499, 562; 422/99
See application file for complete search history.

(56) References Cited

U.S. PATENT DOCUMENTS

| | | | | |
|---|---|---|---|---|
| 1,833,461 A | * | 11/1931 | Grupe | 492/28 |
| 3,354,518 A | * | 11/1967 | Eugene | 24/134 R |
| 3,643,812 A | * | 2/1972 | Mander et al. | 211/74 |
| 4,349,109 A | * | 9/1982 | Scordato et al. | 206/562 |
| 4,928,821 A | * | 5/1990 | Belko, Jr. | 206/728 |

(Continued)

FOREIGN PATENT DOCUMENTS

| | | |
|---|---|---|
| JP | 2003210578 A | 7/2003 |
| JP | 2003210578 A * | 7/2003 |
| WO | 9945985 A1 | 9/1999 |
| WO | 2007099649 A1 | 9/2007 |

OTHER PUBLICATIONS

International Search Report Issued Feb. 12, 2010 in Int'l Application No. PCT/US2009/062226.

(Continued)

*Primary Examiner* — Laura A Bouchelle
*Assistant Examiner* — Scott Medway
(74) *Attorney, Agent, or Firm* — Panitch Schwarze Belisario & Nadel LLP

(57) ABSTRACT

A piston nest (10) is provided that includes a plurality of spaced apart single nesting units (12) interconnected by a web (13). Each of the single nesting units is configured a hollow cylindrical body having a first open end about a distal end of the body and a second open end about the proximal end. The hollow cylindrical body also includes a first (24) and a second (26) retention member for retaining a piston within the single nesting unit. The first and the second retention members are spaced apart along a longitudinal axis of the hollow cylindrical body.

13 Claims, 4 Drawing Sheets

U.S. PATENT DOCUMENTS

| | | | | |
|---|---|---|---|---|
| RE34,133 E | * | 11/1992 | Thorne | 422/553 |
| 5,392,914 A | * | 2/1995 | Lemieux et al. | 206/499 |
| 5,417,329 A | * | 5/1995 | Whitman | 206/499 |
| 5,441,702 A | * | 8/1995 | Lemieux et al. | 422/526 |
| 5,452,810 A | * | 9/1995 | Schwartz | 211/74 |
| 5,516,490 A | * | 5/1996 | Sanadi | 422/552 |
| 5,823,363 A | * | 10/1998 | Cassel | 211/60.1 |
| 5,948,362 A | * | 9/1999 | Steinbrenner et al. | 422/526 |
| 6,164,044 A | * | 12/2000 | Porfano et al. | 53/471 |
| 6,566,144 B1 | * | 5/2003 | Madril et al. | 436/177 |
| 6,719,141 B2 | * | 4/2004 | Heinz et al. | 206/563 |
| 7,060,226 B1 | * | 6/2006 | Jessop et al. | 422/526 |
| 7,927,012 B2 | * | 4/2011 | Harr et al. | 374/158 |
| 8,100,263 B2 | * | 1/2012 | Vanderbush et al. | 206/524.8 |
| 8,168,137 B2 | * | 5/2012 | Powell et al. | 422/500 |
| 2003/0173312 A1 | * | 9/2003 | Real et al. | 211/40 |
| 2005/0040068 A1 | * | 2/2005 | Palder | 206/499 |
| 2006/0016156 A1 | * | 1/2006 | Bush et al. | 53/434 |
| 2009/0277812 A1 | * | 11/2009 | Driscoll | 206/499 |
| 2011/0071475 A1 | * | 3/2011 | Horvath et al. | 604/192 |

OTHER PUBLICATIONS

Int'l Preliminary Report on Patentability issued May 3, 2011 in Int'l Application No. PCT/US2009/062226; Written Opinion.

* cited by examiner

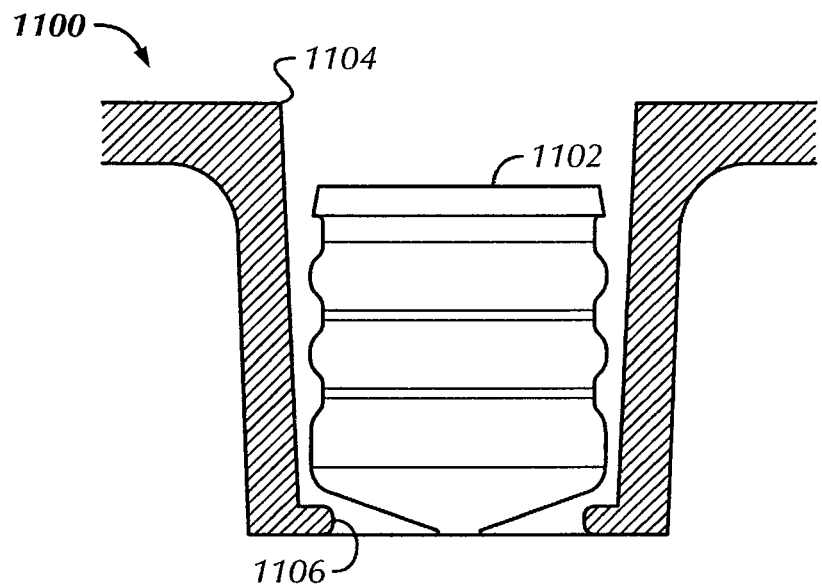
FIG. 1
*(Prior Art)*
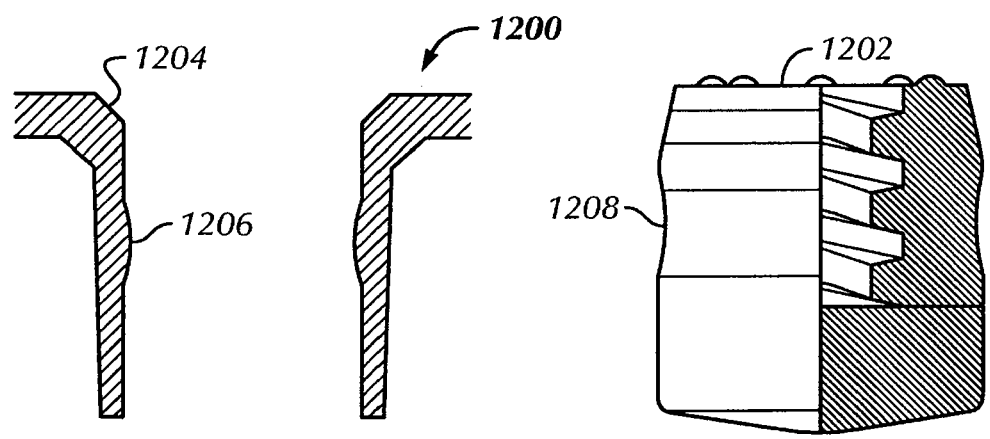
FIG. 2A
*(Prior Art)*
FIG. 2B
*(Prior Art)*

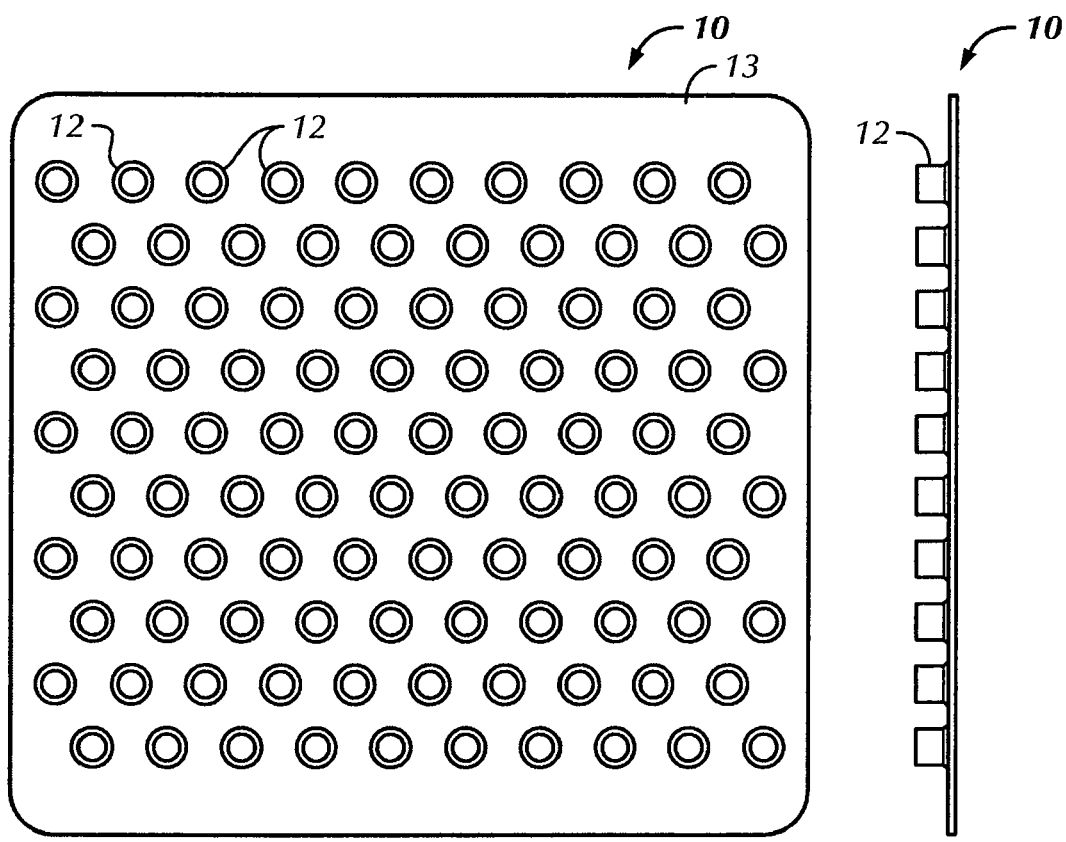
*FIG. 3A*  *FIG. 3B*

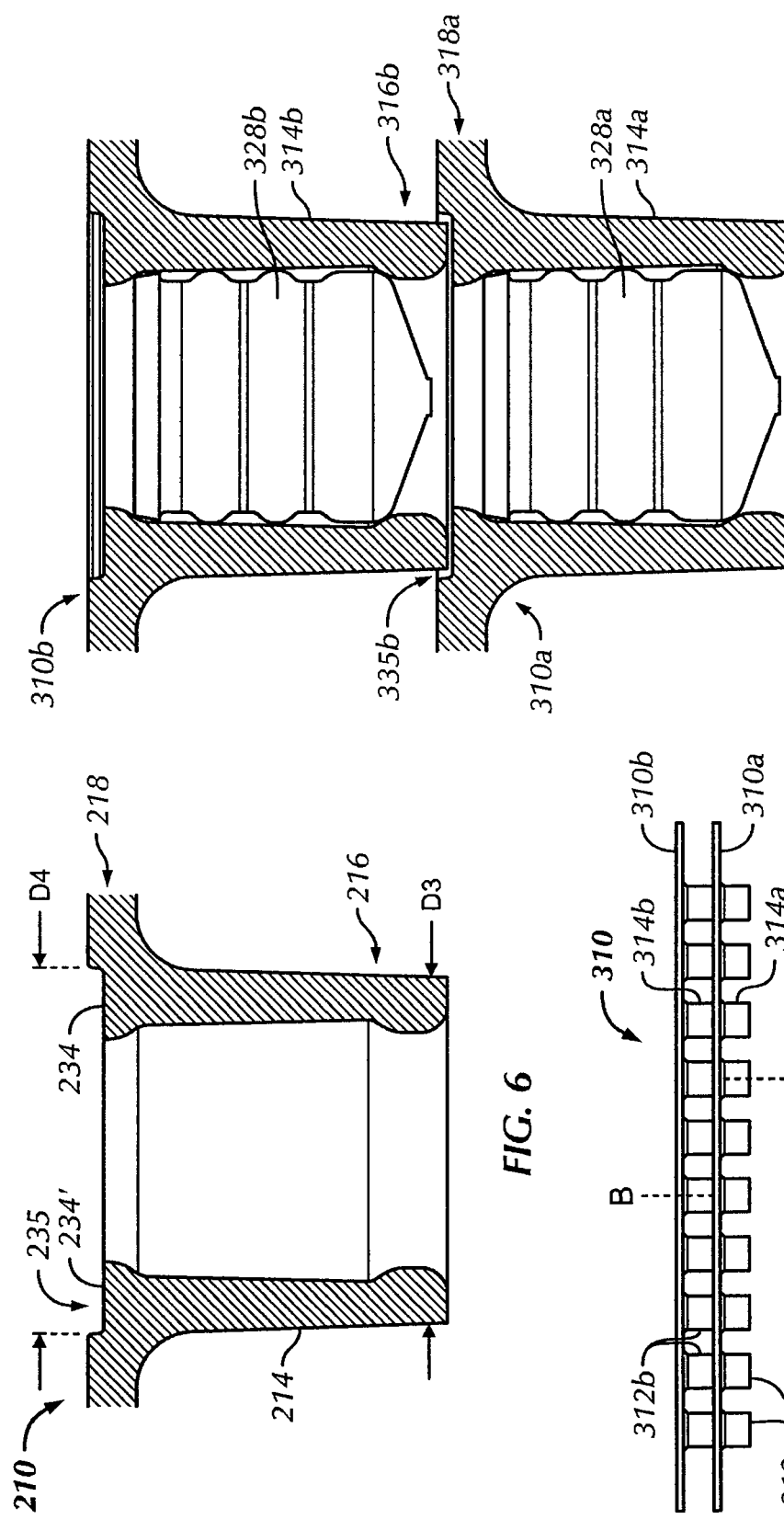

SYRINGE PISTON NEST FOR THE
MANUFACTURE OF PRE FILLED SYRINGE

CROSS-REFERENCE TO RELATED
APPLICATION

This application is a section 371 of International Application No. PCT/US2009/062226, filed Oct. 27, 2009, which was published in the English language on Jun. 3, 2010 under International Publication No. WO 2010/062602 A1 which claims the benefit of U.S. Provisional Patent Application No. 61/108,950, filed Dec. 28, 2008, the disclosure of which are incorporated herein by reference.

BACKGROUND OF THE INVENTION

The present invention relates to a piston nest. In particular, the present invention relates to a piston nest that can securely individually nest a plurality of pistons, such as syringe pistons, prior to automated assembly of the pistons to syringes.

A piston nest is typically a substantially planar tray having a plurality of individual nesting units each capable of receiving a syringe piston. The piston nest is typically used in automation processes for the assembly of e.g., pre-filled syringes. In operation, the piston nest is placed above a similarly oriented tray of pre-filled syringe barrels and then each of the pistons from the piston nest are pressed into the aligned underlying syringe barrels by an automated means, such as with automated mechanical pins. The mechanical pins function to push each of the syringe pistons out of the piston nest and into the underlying individual syringe barrels.

A partial cross-sectional view of an individual nesting unit of a conventional piston nest is shown in FIG. 1. As shown in FIG. 1, the piston nest 1100 is configured such that the syringe piston 1102 rests within a single nesting unit 1104. The syringe piston 1102 is retained within the single nesting unit 1104 by an inwardly extending flange portion 1106 located at the bottom of the piston nesting unit 1104. In such a piston nest configuration, the syringe piston 1102 is only retained within the single nesting unit 1104 by gravity. As such, the piston nest 1100 must be constantly maintained in the proper orientation i.e., the upright position, shown in FIG. 1, in order for the syringe piston 1102 to remain within the single nesting unit 1104. Otherwise, the syringe piston 1102 will be prone to "fall out," become "cocked" or otherwise escape from the single nesting unit 1104. This is especially troublesome when the piston nest 1100 is configured with a large number e.g., one hundred (100) single nesting units per piston nest, which is typically the case. Moreover, in order to properly assemble the syringe piston 1102 into syringe barrels (not shown), the syringe piston 1102 must be properly oriented in the piston nest 1100 i.e., not cocked or otherwise jammed within the single nesting unit 1104.

FIGS. 2A and 2B illustrate another individual nesting unit of a conventional piston nest 1200 and syringe piston 1202 manufactured by Daikyo Seiko, Ltd. The piston nest 1200 however, has a single nesting unit 1204 configured to specifically mate with the Daikyo syringe piston 1202. In particular, the single nesting unit 1204 includes a retention rib 1206 about a midpoint along the length of the nesting unit 1204 which is designed to specifically mate with an annular recess or groove 1208 of the syringe piston 1202. Consequently, the piston nest 1200 cannot be used with any other syringe piston designs besides the Daikyo syringe piston 1202. Moreover, the single nesting unit 1204 is limited to a single point contact retention means for securing the syringe piston 1202 within the piston nest 1200. Such single point contact retention means renders the syringe piston 1202 susceptible to cocking or displacement within the single nesting unit 1204 that may result from mishandling of the piston nest 1200. This is especially important because, for example, with one hundred single nesting units per piston nest 1200, if a single syringe piston 1202 is out of alignment, the entire piston nest 1200 must be discarded. Accordingly, there is still a need for a piston nest that can reliably hold and retain a plurality of syringe pistons and that addresses the above-described deficiencies of conventional piston nests.

BRIEF SUMMARY OF THE INVENTION

In accordance with the present invention, the problem of syringe pistons escaping from or otherwise becoming misaligned within a piston nest is solved by engendering a robust multipoint retention of the syringe piston within the piston nest. In this way, the manufacture of pre-filled syringes can be accomplished in a more reliable and cost-effective manner by eliminating the waste associated with piston nests that would otherwise need to be discarded due to one or more misaligned pistons within the nest.

In a preferred embodiment, the present invention provides a piston nest comprising a plurality of spaced apart single nesting units interconnected by a web. Each nesting unit includes a hollow cylindrical body, a first retention member and a second retention member. The hollow cylindrical body includes a distal end having a first open end and a proximal end having a second open end. The first retention member is proximate the distal end of the hollow cylindrical body. The second retention member is proximate the proximal end of the hollow cylindrical body. Furthermore, the first and the second retention members are spaced apart along a longitudinal axis of the hollow cylindrical body.

In another preferred embodiment, the present invention provides a piston nest assembly comprising at least a first and a second piston nest. Each of the first and the second piston nests comprise a plurality of spaced apart single nesting units interconnected by a web. The single nesting units each include a hollow cylindrical body, a first retention member and a second retention member. The first retention member is proximate the distal end of the hollow cylindrical body. The second retention member is proximate the proximal end of the hollow cylindrical body. The piston nest assembly also includes a piston configured within each of the plurality of spaced apart single nesting units of each of the first and second piston nests. The first and the second piston nests are stacked with a central longitudinal axis of each of the hollow cylindrical bodies of the first piston nest substantially coaxial with a respective central longitudinal axis of each of the hollow cylindrical bodies of the second piston nest. Furthermore, the distal ends of each of the hollow cylindrical bodies of the second piston nest are received within a recess of the corresponding hollow cylindrical bodies of the coaxially aligned first piston nest.

BRIEF DESCRIPTION OF THE SEVERAL
VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is an enlarged, partial, cross-sectional, elevational view of a single nesting unit of a conventional piston nest with a nested syringe piston;

FIG. 2A is an enlarged, partial, cross-sectional, elevational view of a single nesting unit of another conventional piston nest;

FIG. 2B is a partial, cross-sectional, elevational view of a conventional syringe piston compatible with the piston nest of FIG. 2A;

FIG. 3A is a top plan view of a piston nest in accordance with a preferred embodiment of the present invention;

FIG. 3B is an orthographic, side view of the piston nest of FIG. 3A;

FIG. 6 is an enlarged, partial, cross-sectional, elevational view of a single nesting unit of a piston nest in accordance with yet another aspect of the present invention;

FIG. 7 is an elevational view of a piston nest assembly in accordance with another embodiment of the present invention; and FIG. 8 is an enlarged, partial, cross-sectional, elevational view of a portion of the piston nest assembly of FIG. 7.

DETAILED DESCRIPTION OF THE INVENTION

Figure 4:
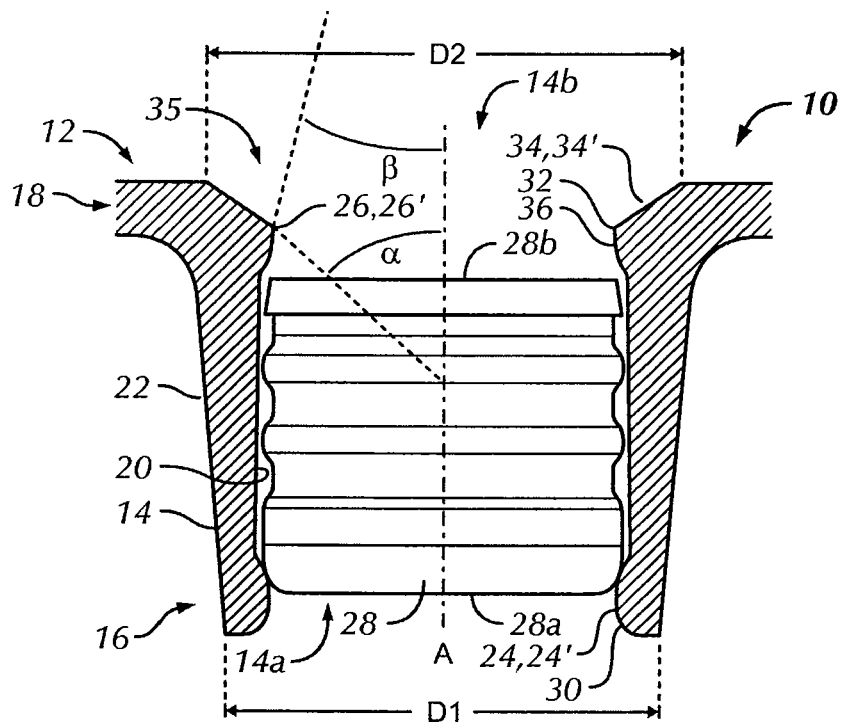
FIG. 4 is an enlarged, partial, cross-sectional, elevational view of a single nesting unit of the piston nest of FIG. 3A with a nested syringe piston.

Reference will now be made in detail to the present embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Unless specifically set forth herein, the terms "a", "an" and "the" are not limited to one element but instead should be read as meaning "at least one". The terminology includes the words noted above, derivatives thereof and words of similar import.

In a preferred embodiment, the present invention provides for a piston nest 10, as shown in FIGS. 3A and 3B. The piston nest 10 includes a plurality of spaced apart single nesting units 12 interconnected by a web 13, as best shown in FIG. 3A. Preferably, the piston nest 10 includes one hundred (100) spaced apart single nesting units 12 (ten by ten as shown), but can be configured to include more or less than one hundred (100). The piston nest 10 can include a piston 28 (FIG. 4) configured within each of the plurality of spaced apart single nesting units 12.

The piston nest 10 is generally configured as a planar tray with the single nesting units 12 connected in a planar fashion by the web 13, as shown in FIGS. 3A-B. While the present embodiment is configured with the piston nest 10 configured as a planar square tray, the piston nest 10 can alternatively be configured into any planar fashion suitable for its intended use, such as a planar circular, rectangular, oval, or octagonal shaped tray.

As best shown in FIG. 4, the single nesting unit 12 includes a generally hollow cylindrical body 14 that extends distally from (below) the web 13, a first retention member 24 and a second retention member 26. The hollow cylindrical body 14 includes a distal end 16 having a first open end 14a (such as an open bottom end) and a proximal end 18 having a second open end 14b (such as an open top end). The hollow cylindrical body 14 also includes a generally smooth interior wall surface 20 and an exterior wall surface 22. The hollow cylindrical body 14 is generally configured such that the interior wall surface 20 tapers radially inwardly toward the distal end 16 so that the diameter of the interior wall surface 20 is at least slightly smaller near the distal end, but can optionally be configured in a cylindrical fashion. The decreasing diameter or taper of the interior wall surface 20 advantageously provides for a smoother transition or travel of the piston 28, such as a syringe piston 28, down the length of the hollow cylindrical body 14 when the syringe piston 28 is being inserted into a syringe barrel (not shown).

The hollow cylindrical body 14 can also optionally be configured such that the exterior wall surface 22 tapers inwardly toward the proximal end 18. Preferably, the hollow cylindrical body 14 is sized such that the internal diameter of the hollow cylindrical body 14 is slightly larger than the overall outside diameter of the syringe piston 28. As such, the hollow cylindrical body 14 facilitates maintaining the syringe piston 28 in the proper orientation i.e., in a non-cocked or un-jammed position, within the hollow cylindrical body 14. The syringe piston 28 is properly aligned within the hollow cylindrical body 14 when a longitudinal axis of the syringe piston 28 substantially aligns with a longitudinal axis A of the hollow cylindrical body 14.

The first retention member 24 is located proximate the distal end 16 of the hollow cylindrical body 14 and is preferably configured as a first radially inwardly extending retention rib 24'. The first retention member 24 can alternatively be configured as an annular rib, a sectional rib, a flange, a flange-like rib, bumps, circumferentially spaced bumps, or the like that extends radially inwardly from the single nesting unit 12 proximate the distal end 16. Preferably, the first retention member 24 is configured such that the syringe piston 28 is supported by the first retention member 24, but can then be forcibly displaced past the first retention member 24. In other words, the first retention member 24 is configured to provide an interference force at least slightly greater than a force generated by the weight of the syringe piston 28. Thus, the first retention member 24 directly contacts a first end 28a of the piston 28, such as a distal end of the piston 28, to provide the interference fit. However, the interference force provided by the first retention member 24 is low enough such that the syringe piston 28 can easily be forcibly pushed through the first open end 14a of the single nesting unit 12. The first retention member 24 is also preferably configured with a rounded surface profile 30 to further facilitate movement of the syringe piston 28 past the first retention member 24. In general, an inner diameter formed by the first retention member 24 is slightly smaller than the overall outer diameter of the syringe piston 28.

The second retention member 26 is located proximate the proximal end 18 of the cylindrical hollow body 14 and preferably configured as a second retention rib 26'. The second retention member 26 is spaced apart from the first retention member 24 along a longitudinal axis A of the hollow cylindrical body 14, preferably a distance at least slightly greater than the length of the piston 28. The second retention member 26 can alternatively be configured as an annular rib, a sectional rib, a flange, a flange-like rib, bumps, circumferentially spaced bumps, or the like that extends radially inwardly from the single nesting unit 12. The second retention member 26 includes an angled surface 32 profile when viewed from a cross-section, as shown in FIG. 4. Preferably, the second retention member 26 has an angled top or upper surface 34 with an angle of α relative to central axis A that is greater than an angled bottom surface 36 of the second retention member 26 having an angle of β relative to central axis A. The angled top surface 34 forms a recess 35, such as a countersink 34', proximate the proximal end 18 of the cylindrical hollow body 14. The recess 35 is in communication with the second open end 14b and forms an upper surface 34 of the second retention member 26. The recess 35 is configured with an overall diameter D2 that is larger than an overall diameter D1 of the distal end of the hollow cylindrical body 14. The angled top surface 34 facilitates the insertion of the syringe piston 28 into the single nesting unit 12. Whereas, the angled bottom surface 36, which preferably is at a smaller angle β relative to angle α, facilitates retention of the syringe piston 28 within the body 14. Preferably, the angle β is about 30 degrees and the angle α is about 45 degrees. As such, the present embodiment advantageously retains the syringe piston 28 within the piston nest 10 when the piston nest 10 is mishandled, such as being inadvertently inverted.

In an alternative embodiment, the piston nest 210 can be configured as shown in FIG. 6. The cylindrical hollow body 214 is substantially configured similar to cylindrical hollow body 14, except for its proximal end 218. Instead of a proximal end having a recess in the form of a countersink, the proximal end 218 of the hollow cylindrical body 214 includes a recess 235 configured as a counterbore 234'. Thus, with a counterbore configuration, the top surface 234 of the cylindrical hollow body 214 is a planar surface. The counterbore 234' has an overall diameter D4 that is larger than an overall diameter D3 of the distal end of the hollow cylindrical body 214 and is configured to receive a distal end 216 of the cylindrical hollow body 214 of a secondary piston nest stacked on top.

Referring back to FIG. 4, the second retention member 26 is spaced apart from the first retention member 24 such that the syringe piston 28 is resting between the first 24 and the second 26 retention members without engaging both the first and the second retention members 24, 26. In other words, the second retention member 26 is spaced apart from a second end 28b of the piston 28 opposite the first end 28a when the first end 28a of the piston 28 is in direct contact with the first retention member 24. That is, the space between the first and the second retention members 24, 26 is at least slightly greater than the height of the piston 28, as shown in FIG. 4.

Figure 5:
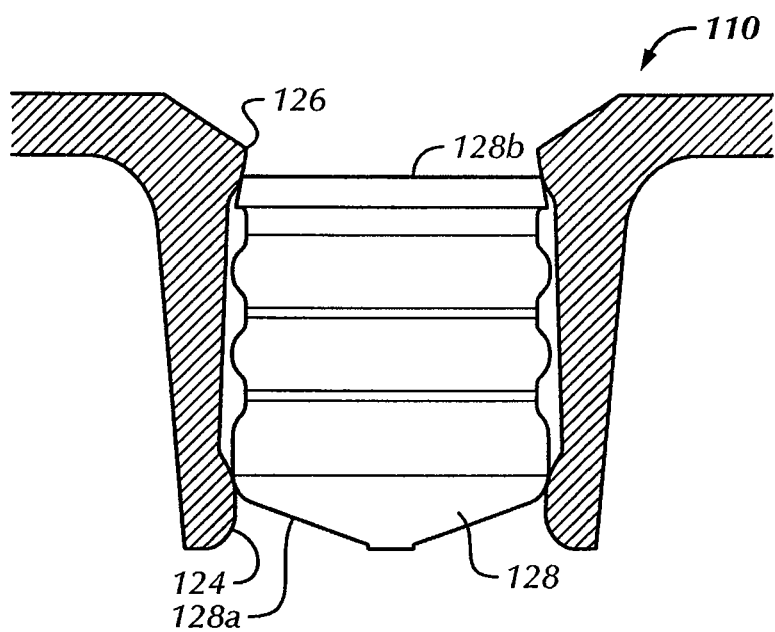
FIG. 5 is an enlarged, partial, cross-sectional, elevational view of a single nesting unit of a piston nest in accordance with another aspect of the present invention with a nested syringe piston.

Alternatively, referring to FIG. 5, in accordance with another embodiment of the present invention, the second retention member 126 of piston nest 110 can be spaced apart from the first retention member 124 such that each of the first and the second retention members 124, 126 are in contact with and provide a coupled retaining force on both a proximal end 128b and a distal end 128a of a syringe piston 128. In other words, the second retention member 126 is in direct contact with a proximal end 128b of the piston 128 opposite the distal end 128a when the distal end 128a of the piston 128 is in direct contact with the first retention member 124. This configuration advantageously provides for a continuous two point contact retention of the syringe piston 128, which further prevents any unnecessary movement of the syringe piston 128 during shipping, handling or otherwise.

A fully assembled piston nest 10 has each single nesting unit 12 occupied by a syringe piston 28. In use, the fully assembled piston nest 10 can be placed above a tray of syringes (not shown), such as pre-filled syringes, in an automated assembly process. With each single nesting unit 12 aligned with a syringe barrel, an automated mechanical push means (not shown), such as a pin, applies a force about the top end 28b of the syringe piston 28 to forcibly move the syringe piston 28 through the first open end 14a (i.e., the bottom open end) of the single nesting unit 12 and into the syringe barrel.

The piston nest 10 can be formed from any rigid material. Preferably, the piston nest 10 is formed from a rigid or a semi-rigid polymeric material, such as high density polyethylene, and more preferably from polypropylene. Polypropylene is preferred as polypropylene piston nests can withstand autoclaving processes better than piston nests formed from other polymeric materials, such as high density polyethylene. Alternatively, as radiation is a preferred method of sterilization, a material which is stable following exposure to standard radiation sterilization processes (e.g., gamma radiation), such as gamma stable polypropylene, is preferred.

In another preferred embodiment, the present invention provides for a piston nest assembly 310, as shown in FIGS. 7 and 8. The piston nest assembly 310 includes at least a first piston nest 310a fully assembled with individual pistons 328a in each of the plurality of spaced apart single nesting units 312a of the first piston nest 310a, and a second piston nest 310b fully assembled with individual pistons 328b in each of the plurality of spaced apart single nesting units 312b of the second piston nest 310b stacked on top of the first piston nest 310a. Each of the first and the second piston nest 310a, 310b can be configured as in any of the above described embodiments. While only a first and a second piston nest 310a, 310b are shown, the piston nest assembly 310 can include any number of piston nests stacked on top of each other as shown. That is, the second piston nest 310b is uniformly stacked (i.e., with edges of each of the first and the second piston nests 310a, 310b aligned) on the first, underlying piston nest 310a such that a central longitudinal axis A of each of the hollow cylindrical bodies 314a of the first piston nest 310a are substantially coaxial with a respective central longitudinal axis B of each of the hollow cylindrical bodies 314b of the second piston nest 310b. As best shown in FIG. 8, the distal end 316b of the hollow cylindrical body 314b of the second piston nest 310b is received within a recess 335b of the proximal end 318a of the hollow cylindrical body 314a of the first piston nest 310a. In other words, the distal ends 316b of each of the hollow cylindrical bodies 314b of the second piston nest 310b are received within the recesses 335b of the corresponding hollow cylindrical bodies 314a of the coaxially aligned first piston nest 310a. As such, the recess 335b provides for a nesting of the secondary piston nest 310b that is stacked on top of a first or underlying primary piston nest.

It will be appreciated by those skilled in the art that changes could be made to the embodiments described above without departing from the broad inventive concept thereof. It is to be understood, therefore, that the present invention is not limited to the particular embodiments disclosed, but it is intended to cover modifications within the spirit and scope of the appended claims.

I claim:

1. A piston nest apparatus for the storage and transport of syringe pistons comprising a piston nest having a plurality of spaced apart single nesting units interconnected by a web and a syringe piston configured within each of the plurality of spaced apart single nesting units, each syringe piston having a first distal end, a second opposing proximal end and a longitudinal length extending therebetween, each nesting unit comprising:

a hollow cylindrical body that includes:

a distal end having a first open end, and
a proximal end having a second open end;
a first retention member proximate the distal end; and
a second retention member proximate the proximal end,
wherein at least a portion of the first and the second retention members are spaced apart at a distance equal to or greater than the longitudinal length of the syringe piston configured within the nesting unit along a longitudinal axis of the hollow cylindrical body, the first retention member being in direct contact with the first distal end of the syringe piston and the second retention member being in direct contact with the second proximal end of the syringe piston.

2. The piston nest apparatus of claim 1, wherein the first and the second retention members are radially inwardly extending members.

3. The piston nest apparatus of claim 2, wherein the first retention member is at least one of a radially inwardly extending flange, rib and plurality of circumferentially spaced bumps.

4. The piston nest apparatus of claim 1, wherein the hollow cylindrical body extends distally from the web.

5. The piston nest apparatus of claim 1, wherein the piston nest comprises one hundred spaced apart single nesting units.

6. The piston nest apparatus of claim 1, wherein the piston nest comprises at least one of a rigid and a semi-rigid polymeric material.

7. The piston nest apparatus of claim 6, wherein the piston nest comprises at least one of a high density polyethylene and a polypropylene.

8. The piston nest apparatus of claim 1, wherein the proximal end of the hollow cylindrical body includes a recess.

9. The piston nest apparatus of claim 8, wherein the recess forms an upper surface of the second retention member.

10. The piston nest apparatus of claim 8, wherein the recess is at least one of a countersink and a counterbore.

11. The piston nest apparatus of claim 8, wherein the recess is in communication with the second open end.

12. The piston nest apparatus of claim 8, wherein the recess has an overall diameter larger than an overall diameter of the distal end of the hollow cylindrical body.

13. A piston nest assembly comprising: at least a first and a second piston nest apparatuses according to claim 8, wherein the first and the second piston nest apparatuses are stacked with a central longitudinal axis of each of the hollow cylindrical bodies of the first piston nest apparatus substantially coaxial with a respective central longitudinal axis of each of the hollow cylindrical bodies of the second piston nest apparatus and the distal ends of each of the hollow cylindrical bodies of the second piston nest apparatus are received within the recesses of the corresponding hollow cylindrical bodies of the coaxially aligned first piston nest apparatus.

* * * * *